United States Patent [19]

Darowski et al.

[11] Patent Number: 4,598,706
[45] Date of Patent: Jul. 8, 1986

[54] APPARATUS FOR INDEPENDENT VENTILATION OF TWO LUNGS WITH SELECTIVE USE OF POSITIVE END-EXPIRATORY PRESSURES

[75] Inventors: Marek Darowski, Warsaw, Poland; Göran Hedenstierna, Djursholm, Sweden

[73] Assignee: Polska Akademia Nauk Instytut Biocybernetyki i Inzynierii Biomedycznej, Warsaw, Poland

[21] Appl. No.: 584,122

[22] Filed: Feb. 27, 1984

[30] Foreign Application Priority Data

Mar. 4, 1983 [PL] Poland .................................. 240878

[51] Int. Cl.$^4$ ............................................ A61M 16/00
[52] U.S. Cl. ........................... 128/205.24; 128/205.23
[58] Field of Search ..................... 128/204.18, 204.23, 128/204.24, 204.25, 204.26, 205.24, 207.14, 207.15, 205.23

[56] References Cited

U.S. PATENT DOCUMENTS 4,233,984 11/1980 Walling .......................... 128/207.14

OTHER PUBLICATIONS

Hedenstierna et al., "Practical Aspects of Differential Ventilation with Selective PEEP in Acute Respiratory Failure", *International Journal of Clinical Monitoring and Computing* (1984), Martinus Nijhoff Publishers, pp. 5–11.

Brown et al., "Improved Ventilation During Thoracotomy with Selective PEEP to the Dependent Lung", *Anesthesia and Analgesia*, vol. 56, No. 1, (1977), pp. 26–31.

Darowski et al., "Development and Evaluation of a Flow-Dividing Unit for Differential Ventilation and Selective PEEP", *Acta Anesthesiol Scand.* 1985, vol. 29, pp. 61–66.

Darowski et al., "A New Control System for Differential Ventilation of the Lungs", Int'l Symposium on Fluid Control and Measurement, Tokyo, 1985, pp. 1–9.

S. Bachrendtz et al: "Differential Ventilation in Acute Bilateral Lung Disease. Influence on Gas Exchange and Central Haemodynamics", Acta Anaesth. Scand. 1983.

N. L. Pace et al.: "Differential Lung Ventilation after Unilateral Hydrochloric Acid Aspiration in the Dog", Critical Care Medicine, vol. 11, No. 1, 1983.

C. P. Dodols et al; "Management of Massive Air Leak with Asynchronous Independent Lung Ventilation", Intensive Care Medicine, 8, 1382.

*Primary Examiner*—Henry J. Recla
*Attorney, Agent, or Firm*—Ladas & Parry

[57] ABSTRACT

An apparatus for controlling and dividing ventilation between lungs during their independent ventilation and connecting only one respirator with the lungs by means of a double-lumen bronchial tube. The apparatus comprises two parallel inspiratory paths and two parallel expiratory paths to separate gas flows between the respiratory and each of the lungs. Each path is connected to the double-lumen bronchial tube through inspiratory and expiratory branches respectively. One of the expiratory paths comprises a positive end-expiratory pressure valve to apply this pressure selectively, to one lung only. A threshold inspiratory valve is placed in one of the inspiratory paths having a common point with the expiratory path not containing the positive end-expiratory pressure valve. This threshold valve is connected in series with a pneumatic unidirectional valve and divides ventilation between the lungs and patterns optimal inspiratory flows. Pneumatic unidirectional valves are situated in both inspiratory and expiratory paths to prevent mixing of gases flowing through these paths.

2 Claims, 1 Drawing Figure

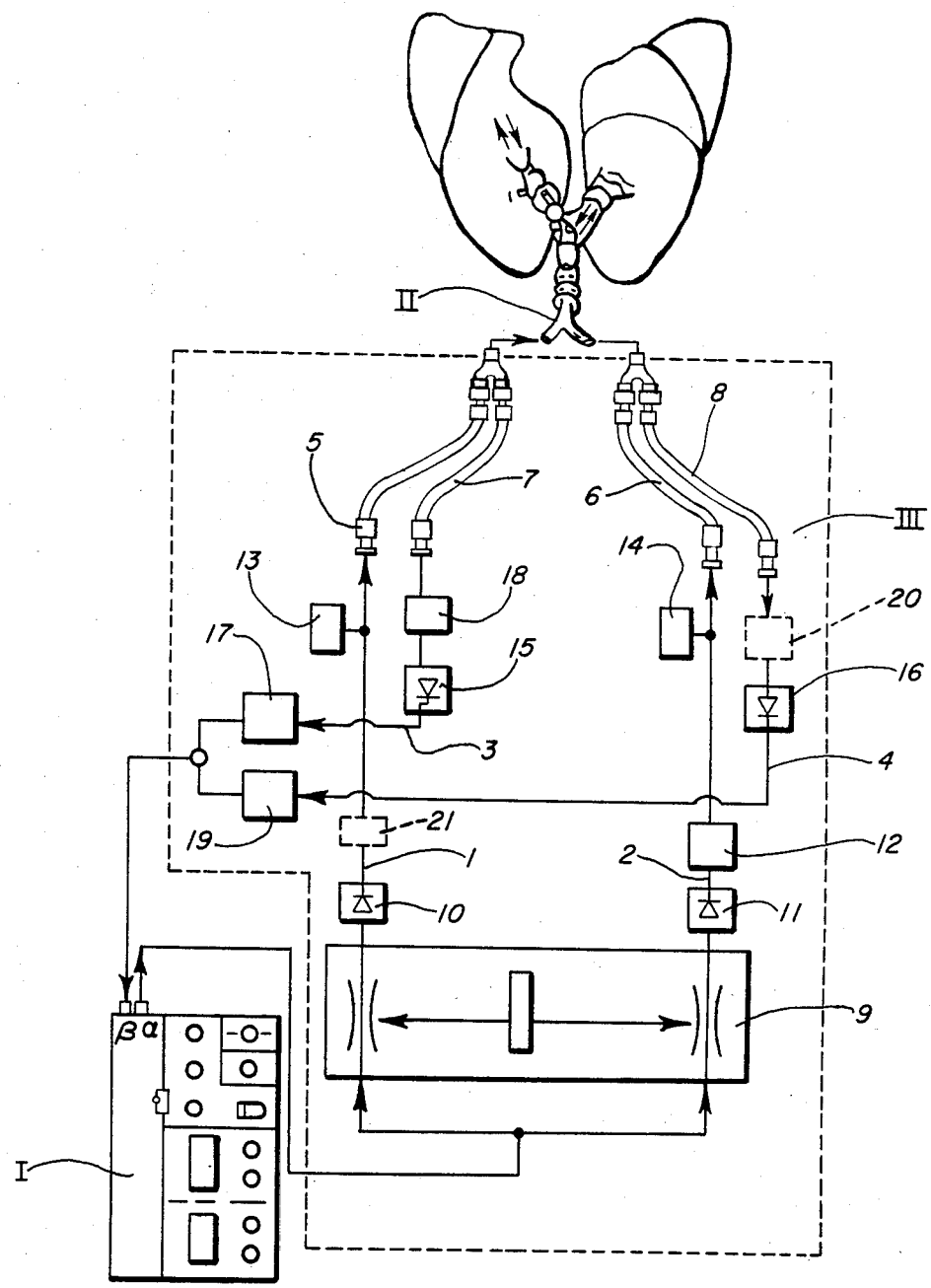

APPARATUS FOR INDEPENDENT VENTILATION OF TWO LUNGS WITH SELECTIVE USE OF POSITIVE END-EXPIRATORY PRESSURES

This invention relates to apparatus for independent ventilation of two lungs with selective use of positive end-expiratory pressures.

Independent ventilation of two lungs with selective use of positive end-expiratory pressures consists in selection of inspiratory volumes and positive end-expiratory pressures for each of lungs in such a way that their ventilation will be adapted to their perfusion. This method of artificial ventilation ensures better, more effective gas exchange in the lungs during intensive care of patients with acute respiratory disease synchroms than in the case of non-controlled division of inspiratory volume between lungs and use of equal values of positive end-expiratory pressures for both lungs.

Known apparatus for independent ventilation of two lungs with selective use of positive expiratory pressures contains generally two synchronized respirators coupled with lungs by means of a double-lumen bronchial tube, through inspiratory and expiratory branches. Those branches are connected together in two inspiratory-expiratory pairs, each comprising inspiratory and an expiratory branch terminating in common point connected with the bronchial tube. One inspiratory-expiratory pair is connected with one of two conduits of this tube, while second pair with other conduit of bronchial tube.

Apparatus for independent ventilation of two lungs with selective use of positive end-expiratory pressures according to the invention connecting only one respirator with the double-lumen bronchial tube comprises two parallel inspiratory paths and two parallel expiratory paths. Each path is coupled with the double-lumen bronchial tube respectively through the inspiratory and expiratory branches. In one inspiratory path having common point with the expiratory path not provided with a positive end-expiratory pressure valve, a threshold inspiratory valve is placed, connected in series with a pneumatic unidirectional valve.

A pneumatic unidirectional valve is also situated in the inspiratory path having common point with the expiratory path provided with the positive end-expiratory pressure valve.

In both inspiratory paths coupled pneumatic resistors interconnected in parallel are placed.

In the another embodiment two threshold inspiratory valves are placed, in one inspiratory path one threshold inspiratory valve respectively. In each inspiratory path the inspiratory threshold inspiratory valve is connected in series with the pneumatic unidirectional valve. In both expiratory paths the positive end-expiratory pressure valves, are placed.

Moreover, in both inspiratory paths coupled pneumatic resistors interconnected in parallel, are placed in case of need.

The apparatus being the object of invention eliminates the necessity of use of two respirators for realization of independent ventilation of two lungs with the application of positive end-expiratory pressures. Such ventilation is realized using only one respirator.

Object of the invention will be explained in detail in example of preferred embodiment given in a drawing displaying the diagram of the apparatus for independent ventilation of two lungs with selective use of positive end-expiratory pressures.

This apparatus III connects a respirator I with lungs by means of a double-lumen bronchial tube II. The apparatus III contains two parallel inspiratory paths 1 and 2, as well as two parallel expiratory paths 3 and 4. The inspiratory and expiratory paths terminate in respectively in inspiratory 5 and 6 as well as in expiratory 7 and 8 branches, connected in inspiratory-expiratory pairs. In each pair the inspiratory branch 5 with the expiratory branch 7 and the inspiratory branch 6 with the expiratory branch 8 are interconnected. A common point of the inspiratory branch 5 and the expiratory branch 7 is coupled with one of two conduits of the double-lumen bronchial tube II, while a common point of the inspiratory branch 6 and the expiratory branch 8 is coupled with a second conduit of the bronchial tube II.

In the inspiratory paths 1 and 2 connected in parallel coupled pneumatic resistors 9 are placed. The pneumatic resistor in the inspiratory path 1 is connected in series with a pneumatic unidirectional valve 10 and the inspiratory branch 5, while the pneumatic resistor in the inspiratory path 2 is connected in series with a pneumatic unidirectional valve 11, a threshold inspiratory valve 12 and the inspiratory branch 6. In the inspiratory paths 1 and 2 pressure gauges 13 and 14 are placed. In expiratory paths 3 and 4 connected in parallel pneumatic unidirectional valves 15 and 16 are placed. The unidirectional valve 15 is connected in series with a volume meter 17, a positive end-the expiratory pressure valve /PEEP/ 18 and expiratory branch 7, while the unidirectional valve 16 is connected in series with a volume meter 19 and the expiratory branch 8.

A common input of the coupled pneumatic resistors 9 is connected with an inspiratory port $\alpha$ of the respirator while a common output of the volume meters 17 and 19 is connected with an expiratory port $\beta$ of the respirator.

The apparatus according to the invention operates as follows. In the inspiratory phase gas outflowing from the inspiratory port $\alpha$ of the respirator is divided between two inspiratory paths 1 and 2 and flows through the coupled pneumatic resistors 9 and the pneumatic unidirectional valves 10 and 11. Gas flowing through the inspiratory path 1 is directed by means of the inspiratory branch 5 and one of conduits of the bronchial tube to one lung, as during inspiratory phase the expiratory port $\beta$ of the respirator is closed. Gas flowing through the inspiratory path 2 and the threshold inspiratory valve 12 is directed by means of the inspiratory branch 6 and a second conduit of the bronchial tube II to the other lung. The increase of pressure in the inspiratory branches 5 and 6 during inspiratory phase is measured and indicated by the pressure gauges 13 and 14, respectively. During expiratory phase the inspiratory port $\alpha$ of the respirator is closed, while the expiratory port $\beta$ of the respirator is open, resulting in outflow of gases from the lungs. And so gas flows from the one lung through one of conduits of the bronchial tube II via expiratory branch 7, the positive end-expiratory pressure valve /PEEP/ 18, the pneumatic unidirectional valve 15, and the volume meter 17 down to the expiratory port $\beta$ of the respirator. On the other hand gas flows from the second lung through second conduit of the bronchial tube II via expiratory branch 8, pneumatic unidirectional valve 16 and the volume meter 19 down to the expiratory port $\beta$ of the respirator. The pneumatic unidirectional valves 10, 11, 15, 16 placed in definite places of examined system of connections of the apparatus according to the invention determinate the desired direction of a flow of gases, as described above, between the respirator and the lungs in individual phases of end-respiratory cycle /i.e. during inspiratory and expiratory phases/, enabling both the realization of independent ventilation of each lung and establishing positive end-expiratory pressure in one of the lungs only /by means of PEEP 18 valve/. The threshold inspiratory valve 12 placed in the inspiratory path 2 of the second lung divides ventilation between the lungs and compensate the change of gas flow rate during the inspiratory phase in inspiratory path 1, occuring after introduction of a positive end-expiratory pressure by means of PEEP valve 18, or during dynamic changes of the values of mechanical parameters of a patient respiratory system. The aim of the threshold valve 12 is also to pattern different inspiratory gas flows to each lung, which according to clinical findings, are optimal for gas exchange in the lungs in cases of acute respiratory failure of a patient. Thus a gas flow through the inspiratory path 1 has a decreasing pattern during an inspiratory phase, and a gas flow through the inspiratory path 2 has an increasing one. By means of coupled pneumatic resistors 9 the gas flow may be diminished in one inspiratory path, and at the same time increased in the other one.

In another embodiment the apparatus according to the invention is additionally provided with a positive end-expiratory pressure valve PEEP 20, used for setting the positive end-expiratory pressure in the expiratory branch 8 /and therefore in the lung coupled with this branch through the conduit of the bronchial tube/, and also provided with a threshold inspiratory valve 21, compensating the changes of gas flow rate during inspiratory phase in the inspiratory path 2.

The above embodiment apart from the possibility of providing an independent ventilation of each lung enables the application of a positive end-expiratory pressures independently to both lungs.

We claim:

1. An apparatus for controlling and dividing ventilation between two lungs with selective use of positive end-expiratory pressures, comprising: a single respirator, a double-lumen bronchial tube, conduit means connecting means respirator with the lungs by means of said double-lumen bronchial tube, said conduit means including two inspiratory and two expiratory branches connected in two inspiratory-expiratory pairs, each pair being terminated by a common point of the inspiratory and expiratory branches and being coupled with one of two conduits of the double-lumen bronchial tube, said double-lumen bronchial tube together with the two parallel inspiratory branches and two parallel expiratory branches including means adapted to separate gas flows between the respirator and each lung respectively, one of the said expiratory branches being provided with a positive end-expiratory pressure valve to apply this pressure selectively to one lung only, a threshold inspiratory valve to control the distribution of ventilation between the lungs and to pattern an increasing gas flow through one inspiratory branch and a decreasing inspiratory gas flow through the other inspiratory branch, said threshold inspiratory valve being placed in one inspiratory branch having a common point with the expiratory branch not provided with the positive end-expiratory pressure valve, a pneumatic unidirectional valve being placed in said one inspiratory branch, said threshold inspiratory valve being connected in series with a pneumatic unidirectional valve to prevent mixing of gases flowing through said inspiratory branches, another pneumatic unidirectional valve being placed in the second inspiratory branch to prevent mixing of gases flowing therethrough, one pneumatic unidirectional valve being placed in each expiratory branch to enable an independent measurement of volumes of gas expired from each lung and a total ventilation measurement by the respirator, a variable pneumatic resistor being placed in each of said inspiratory branches, and means interconnecting said resistors to inversely vary the flow through each resistor, respectively, in order to diversify to the maximum the amount of ventilation to each lung.

2. An apparatus for controlling and dividing ventilation between two lungs with selective use of positive end-expiratory pressures, comprising a single respirator, a double-lumen bronchial tube, conduit means connecting said respirator with the lungs by means of said double-lumen bronchial tube, said conduit means including two inspiratory and two expiratory branches connected in two inspiratory-expiratory pairs, each pair being terminated by a common point of the inspiratory and expiratory branches and being coupled with one of the two conduits of the double-lumen bronchial tube, said double-lumen bronchial tube together with the two parallel inspiratory branches and two parallel expiratory branches including means adapted to separate gas flows between the respirator and each lung respectively, at least one of said inspiratory branches having a threshold inspiratory valve to control distribution of ventilation between the lungs and to pattern different inspiratory gas flows to each lung, said inspiratory and expiratory branches having pneumatic unidirectional valves, respectively, one in each branch to prevent mixing of gases flowing through these branches, two positive end-expiratory valves, one placed in each of said expiratory branches, respectively, to apply different positive end-expiratory pressures to each lung a variable pneumatic resistor being placed in each of said inspiratory branches, and means interconnecting said resistors to inversely vary the flow through each resistor, respectively, in order to diversify to the maximum the amount of ventilation to each lung.

* * * * *